US00PP27479P2

(12) United States Plant Patent
MacGregor et al.

(10) Patent No.: US PP27,479 P2
(45) Date of Patent: Dec. 20, 2016

(54) ***ANEMONE HYBRIDA* PLANT NAMED 'MACANE015'**

(50) Latin Name: *Anemone hybrida*
Varietal Denomination: Macane015

(71) Applicants: Alasdair MacGregor, Kirkcudbright (GB); Elizabeth MacGregor, Kirkcudbright (GB)

(72) Inventors: Alasdair MacGregor, Kirkcudbright (GB); Elizabeth MacGregor, Kirkcudbright (GB)

( * ) Notice: Subject to any disclaimer, the term of this patent is extended or adjusted under 35 U.S.C. 154(b) by 0 days.

(21) Appl. No.: 14/756,784

(22) Filed: Oct. 13, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — Samuel R. McCoy, Jr.

(57) ABSTRACT

'Macane015' is a new and distinctive variety of *Anemone hybrida* which is characterized by a compact growth habit, flowers with a high number of tepals arranged in a tight rosette, flowers with unique dark pink to red-purple coloration, and an exceptionally long bloom period. The new variety propagates successfully by stem cuttings and tissue culture and has shown to be uniform and stable in the resulting generations from asexual propagation.

3 Drawing Sheets

Latin name of the genus and species: The Latin name of the genus and species of the novel variety disclosed herein is *Anemone hybrida*.

Variety denomination: The inventive variety of *Anemone hybrida* disclosed herein has been given the variety denomination 'Macane015'.

BACKGROUND OF THE INVENTION

The present invention relates to a new and distinct cultivar of *Anemone hybrida*, which has been given the variety denomination of 'Macane015'. Its market class is PLT/263.1.

Parentage: 'Macane015' is the result of a controlled cross-pollination breeding program carried out by the inventors at their commercial nursery in Kirkcudbright, Scotland, in 2008. The inventors performed a controlled cross-pollination of the emasculated mother plant, *Anemone hupehensis* var. *japonica* 'Pamina' (unpatented) with the pollen parent, an unnamed *Anemone hybrida* seedling developed by the inventors (unpatented). Said pollination was performed in an insect proof environment. Seed from said cross was harvested, then germinated, and the resulting seedlings were then grown to a mature size in a protected poly tunnel greenhouse. In July of 2008, the inventors selected the new *Anemone* cultivar due to its compact growth habit and unique flower and bloom characteristics. This new and distinctive cultivar was given the name 'Macane015'.

Asexual Reproduction: Asexual reproduction of 'Macane015' was first accomplished in 2008 by way of root cuttings at the inventor's nursery in Kirkcudbright, Scotland. After several years of experimentation, 'Macane015' was also asexually reproduced by way of meristematic tissue culture micropropagation at a plant tissue culture laboratory in the Netherlands. Successive generations produced from both root cuttings and tissue culture have shown that the unique features of the instant cultivar are stable and reproduce true to type.

SUMMARY OF THE INVENTION

The cultivar 'Macane015' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Anemone hybrida* cultivar, 'Macane015'. These traits, in combination, distinguish 'Macane015' as a new and distinct cultivar.

1. *Anemone* 'Macane015' exhibits a compact growth habit.
2. *Anemone* 'Macane015' exhibits unique dark pink to red-purple coloration of the flower.
3. *Anemone* 'Macane015' exhibits flowers with tepals arranged in a tight rosette; and
4. *Anemone* 'Macane015' exhibits flowers with a high tepal count; and
5. *Anemone* 'Macane015' exhibits an exceptionally long bloom period, from July until the end of autumn when grown outdoors in the Netherlands.

BOTANICAL DESCRIPTION OF THE PLANT

Figure 1:
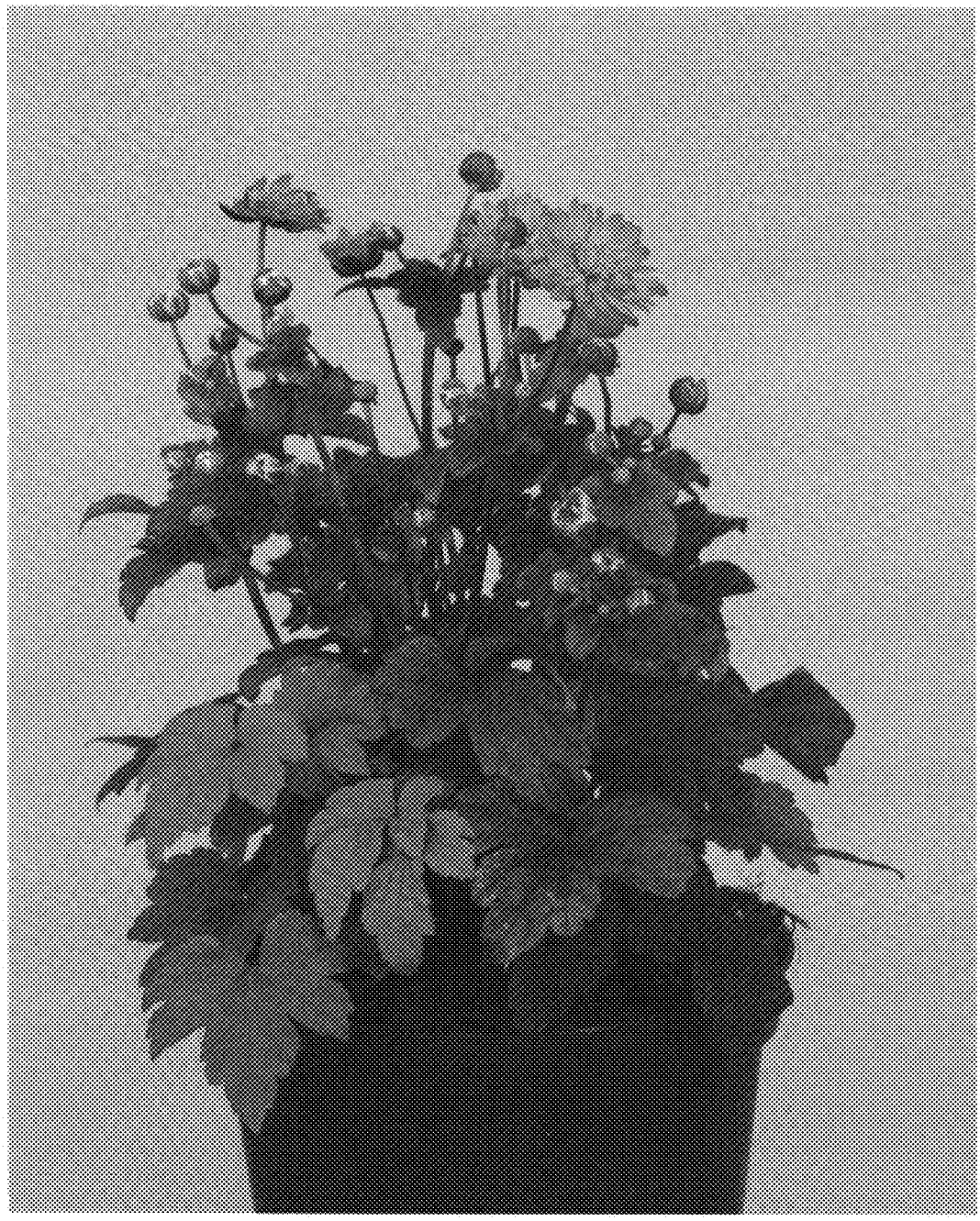
FIG. 1 shows, as nearly true as it is reasonably possible to make the same in color illustrations of this type, the typical foliage and growth characteristics of the new cultivar, 'Macane015'. The plant shown is approximately 15 months old from a rooted cutting, potted into an 18 cm nursery pot, grown outdoors in Kirkcudbright, Scotland at a commercial nursery.
Figure 2:
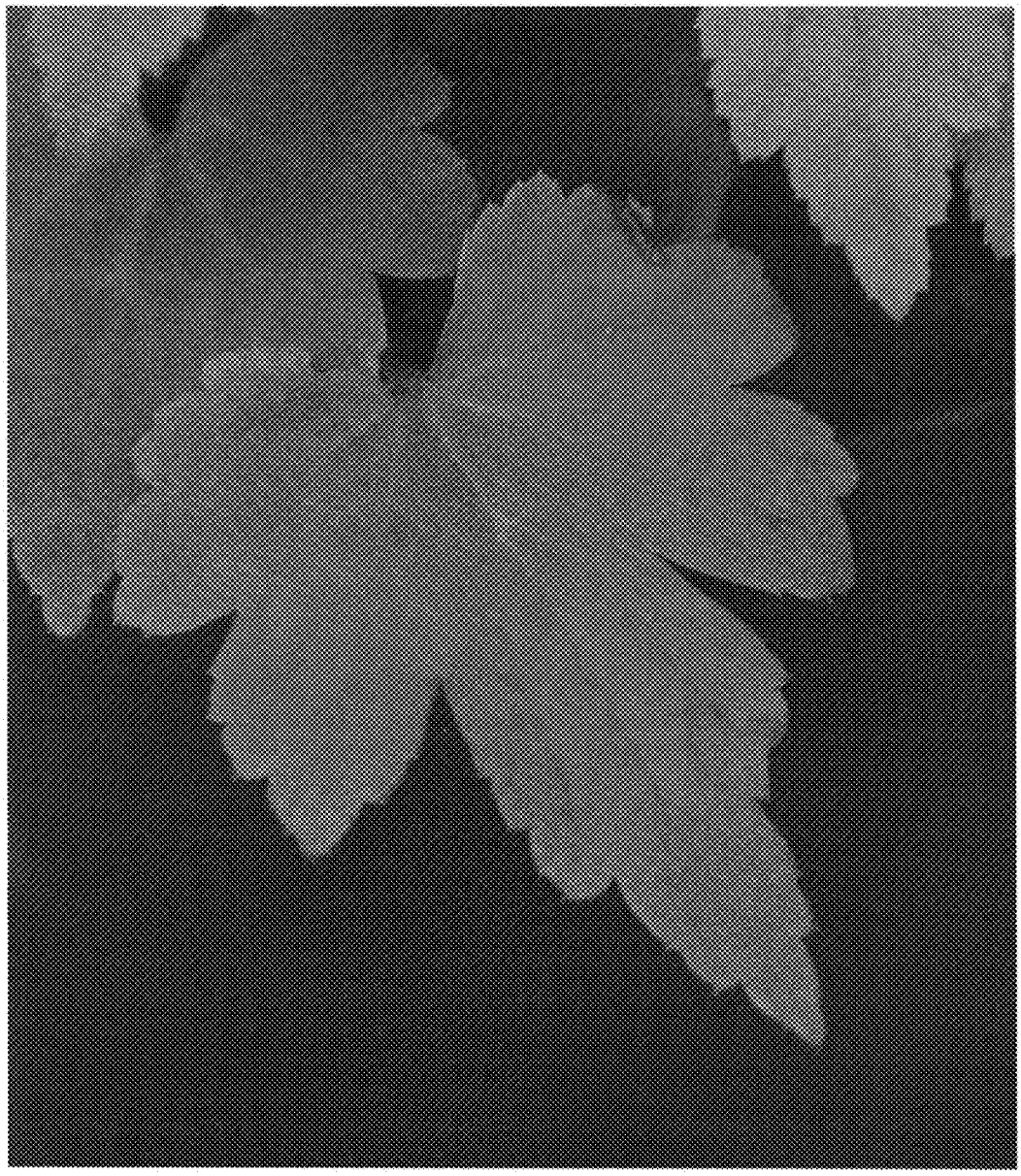
FIG. 2 shows, as nearly true as it is reasonably possible to make the same in color illustrations of this type, the typical foliage of the plant in FIG. 1.
Figure 3:
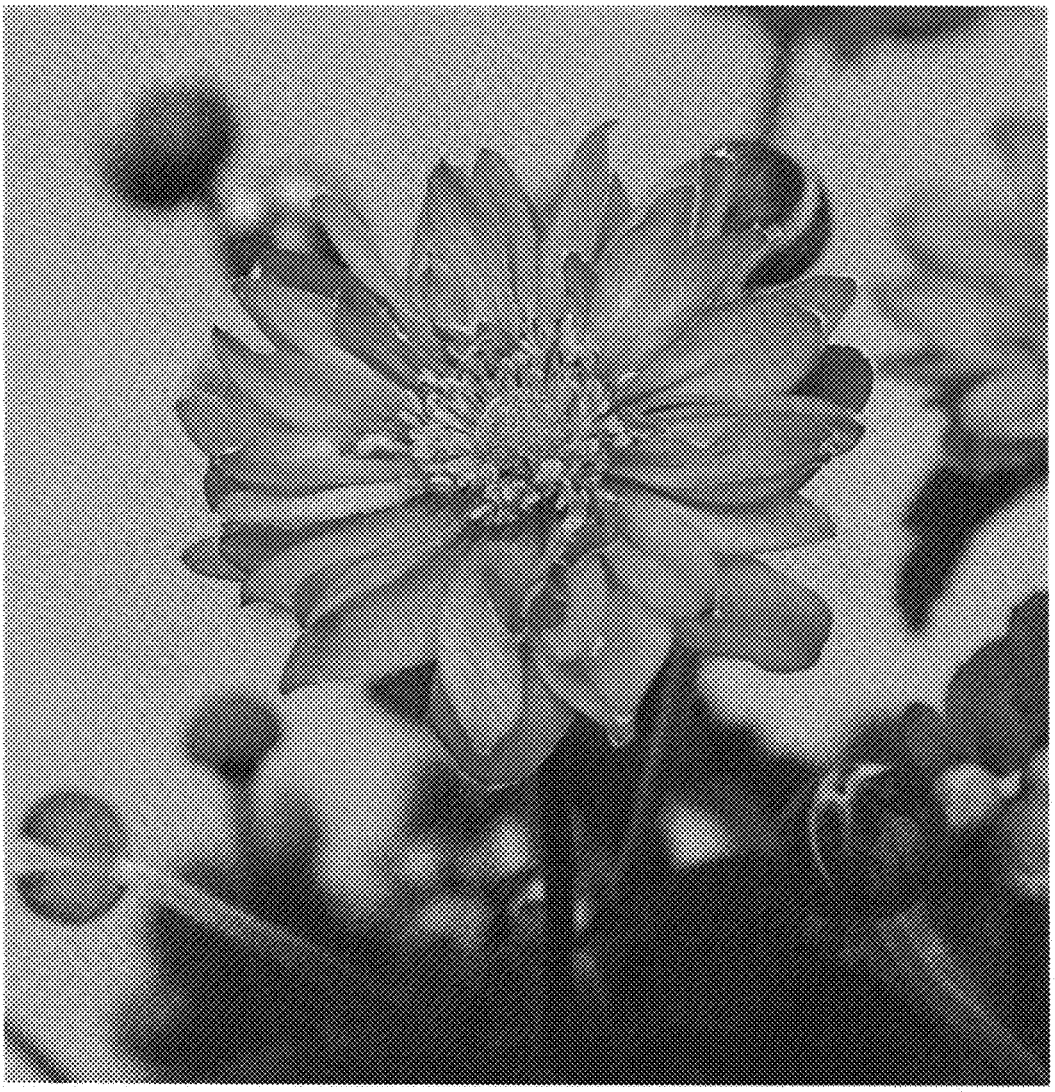
FIG. 3 shows, as nearly true as it is reasonably possible to make the same in color illustrations of this type, the typical flower of the plant in FIG. 1.

The following is a detailed botanical description of a new and distinct variety of *Anemone hybrida* known as 'Macane015', based upon observations of plants, approximately 15 months old from a rooted cutting, potted into an 18 cm nursery pot and grown outdoors in Kirkcudbright, Scotland at a commercial nursery. Temperatures ranged from 8 to 22 degrees Celsius during the day and 0 to 12 degrees Celsius at night. During the winter period, from December to March, plants were sheltered in a large polytunnel with day temperatures ranging from 5 to 18 degrees Celsius, and night temperatures ranging from minus-5 to positive-8 degrees Celsius. No artificial light, photoperiodic treatments or chemical treatments were given to the plants. Observation data was recorded in August of 2015.

Those skilled in the art will appreciate that certain characteristics will vary with older or, conversely, with younger plants. 'Macane015' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2007 edition.

A botanical description of 'Macane015' and comparisons with the parents and most similar variety of common knowledge are provided below.

General plant description:

*Growth rate*.—Low to moderate.

*Growth habit*.—Herbaceous perennial; upright and compact plant habit with leaves developing from basal rosettes; flowering stems arising from the rosette also bear foliage; no lateral branching is present.

*Height*.—25.5 cm in height.

*Width*.—30.9 cm in width.

*Hardiness*.—Hardy to at least USDA Zone 6.

*Propagation*.—Root cuttings and tissue culture.

*Time to produce flowering plant from rooted cutting*.—Approximately 9 to 12 months.

*Pest resistance and susceptibility*.—Not any more or less susceptible to pests or diseases known to effect *Anemone*.

Root system: Thin, non-fibrous, non-fleshy; color is near RHS 164B.

Foliage:

*Arrangement*.—Basal rosette; pedunculate leaves are also present.

*Type*.—Simple; occasionally compound with three leaflets.

*Quantity*.—Approximately 10 leaves per basal rosette; quantity of pedunculate leaves varies.

*Attachment*.—Petiolate.

*Petiole*.—Length — Average of 86 mm. Diameter — Average of 1.5 mm. Color — Near RHS 143B, darker towards the base, near RHS 146B, and proximal end strongly tinged near RHS N186C. Texture — Moderately covered with short hairs; average length of hairs is 0.5 mm; colored near RHS 155D.

*Stipule*.—Length — Average of 8 mm. Diameter — Average of 3 mm. Color — Near RHS 147D. Texture — Moderately covered with short hairs; average length of 0.5 mm; colored near RHS 155D.

*Lamina, trilobate leaves*.—Dimensions — 9.0 cm long and 7.4 cm in width, on average. Leaf attitude — Leaves in an average angle of 70° to stem (=0). Leaf shape — Trilobate. Leaf apex — Acute. Leaf base — Hastate to very short attenuate. Leaf margin — Serrate to Biserrate. Texture, adaxial surface — Slightly glossy. Pubescence, adaxial surface — Moderately covered with short appressed hairs with an average length of 0.5 mm; colored near RHS 157D. Pubescence, abaxial surface — Main veins and secondary veins moderately covered with an average length of 0.5 mm; colored near RHS 157D. Color — Juvenile foliage color, adaxial surface — Near RHS 143A. Juvenile foliage color, abaxial surface — In between near RHS 143C and 144A. Mature leaf color, adaxial surface — Near RHS NN137A. Mature leaf color, abaxial surface — Near RHS 147B. Venation — Pinnate. Vein color, adaxial surface — Near RHS 143A to 143B. Vein color, abaxial surface — Near RHS 144A.

*Leaflets, trifoliate leaves*.—Attitude — Leaves in an average angle of 70° to stem (=0). Shape — Ovate. Apex — Acute. Base — Hastate to very short attenuate. Leaf margin — Serrate to Biserrate. Texture, adaxial surface — Slightly glossy. Pubescence, adaxial surface — Same as lamina of the simple leaves. Pubescence, abaxial surface — Same as lamina of the simple leaves. Color — Coloration of both juvenile and mature leaflets is the same the simple leaves. Venation — Venation of leaflets is the same as the venation of the simple leaves.

Inflorescence:

*Habit*.—Terminal corymb.

*Natural flowering season*.—Midsummer to late summer.

*Peduncles*.—Length — Average of 184 mm. Diameter — Average of 3.5 mm. Angle — Average angle to basal rosette is approximately 80°. Strength — Moderately strong. Texture — Slightly glossy; densely covered with short soft hairs; average length of hairs is 0.75 mm; colored near RHS 156D. Color — Near RHS 146B; strongly tinged near RHS N200A. Pedunculate leaves — All characteristics of the pedunculate leaves are approximately the same as those of the rosette.

*Pedicels*.—Length — Average of 75 mm. Diameter — Average of 2 mm. Angle — Average angle to peduncle is approximately 65°. Strength — Moderately strong. Texture — Slightly glossy; densely covered with short soft hairs; average length of hairs is 0.75 mm; colored near RHS 156D. Color — Near RHS 146B; strongly tinged near RHS N200A.

Bud:

*Shape*.—Globular to flattened globular.

*Length*.—Average of 8 mm.

*Diameter*.—Average of 9 mm.

*Color*.—In between near RHS N186C and 200A to 200B, base near RHS 149B.

Flower:

*Shape, habit*.—Rotate; perianth consisting of multiple whorls of tepals.

*Aspect*.—Upright to slightly outward.

*Rate of flower opening*.—14 to 21 days from bud to fully opened flower.

*Flower longevity on plant*.—Approximately one week.

*Persistent or self-cleaning*.—Self-cleaning.

*Fragrance*.—Non-fragrant.

*Diameter*.—Average of 48 mm.

*Depth*.—Average of 14 mm.

*Tepals*.—Quantity — Approximately 48. Arrangement — Rotate; tight rosette. Length — 20 mm, on average. Width — 8 mm, on average. Shape — Obovate. Apex — Obtuse to bluntly acute. Base — Broad Cuneate. Margin — Entire.

*Texture, upper surface*.—Upper surface glabrous, matte, moderately velvety.

*Texture, upper surface*.—Moderately to densely covered with short appressed hairs; average length of hairs is 0.75 mm; colored near RHS 156B to 156D.

*Color*.—When opening, upper surface — Near RHS N75A, darker towards the apex; near RHS 77B, base lighter; near RHS 76B to 76C. When opening, lower surface — Near RHS 70B, base near RHS 156A to 156B. Fully opened, upper surface — Near RHS 72C, darker at the apex; near RHS 71A, base lighter; near RHS 76C to 76D. Fully opened, lower surface — Near RHS 73B, base near RHS 156A to 156B.

Reproductive organs:

*Stamens*.—Quantity — 120, on average. Anthers — Shape — Elliptic. Length — Approximately 2 mm. Color — Near RHS 14A. Filaments — Length — 4 mm, on average. Color — Near RHS 160C to 160D. Pollen — Color — Near RHS 14A. Quantity — Very low.

*Pistil*.—Quantity — 250, on average. Length — 1.25 mm. Style — Length — 1 mm. Color — Near RHS 144B. Stigma — Shape — Club-shaped. Color — Near RHS N144B. Ovary Color — Near RHS 146B.

Seed and fruit: No fruit or seeds have been detected to date.

Comparisons with the Parent Plants

Plants of the new cultivar 'Macane015' may be distinguished from its seed parent, *Anemone hupehensis* var. *japonica* 'Pamina', by the following combination of characteristics:

1. 'Macane015' exhibits a more compact growth habit, with inflorescence reaching approximately 25 to 40 cm tall, whereas 'Pamina' exhibits a taller plant height with inflorescence reaching 60 to 80 cm tall.
2. 'Macane015' exhibits a smaller flower with a tighter rosette and a higher tepal count when compared to that of 'Pamina'.
3. 'Macane015' exhibits a deep-pink flower color, whereas 'Pamina' exhibits a pale pink flower color.

The pollen parent, an unnamed *Anemone hybrida* seedling developed by the inventors, was never commercialized and is no longer in cultivation. Therefore, a comparison with the pollen parent is not available.

Comparisons with the Most Similar Variety of Common Knowledge

Plants of the new cultivar 'Macane015' may be distinguished from the commercial variety, *Anemone hybrida* 'Seranade', by the following combination of characteristics:

1. 'Macane015' exhibits a significantly more compact growth habit, with inflorescence reaching approximately 25 to 40 cm tall, whereas 'Seranade' exhibits a tall plant height with inflorescence reaching 90 to 100 cm tall.
2. 'Macane015' exhibits a smaller flower size with approximately 48 tepals arranged in a tight rosette, whereas 'Seranade' exhibits a large, saucer-shaped flower size with approximately 10 to 14 petals.
3. 'Macane015' exhibits a deep-pink flower color, whereas 'Seranade' exhibits a rose pink flower color.

That which is claimed is:

1. A new and distinct variety of *Anemone hybrida* plant named 'Macane015', substantially as described and illustrated herein.

* * * * *